United States Patent
Bigonzi-Jaker et al.

(10) Patent No.: US 6,240,968 B1
(45) Date of Patent: Jun. 5, 2001

(54) MEMBRANES SUITABLE FOR MEDICAL USE

(75) Inventors: Anna Maria Bigonzi-Jaker; Marc L. Jaker, both of New Brighton, MN (US)

(73) Assignee: RTC, Inc., West St. Paul, MN (US)

( * ) Notice: Subject to any disclaimer, the term of this patent is extended or adjusted under 35 U.S.C. 154(b) by 0 days.

(21) Appl. No.: 08/911,469

(22) Filed: Aug. 14, 1997

Related U.S. Application Data

(60) Provisional application No. 60/023,405, filed on Aug. 14, 1996, and provisional application No. 60/030,589, filed on Nov. 14, 1996.

(51) Int. Cl.[7] .................. F16L 9/18; F16L 11/00; A61F 13/00
(52) U.S. Cl. .................. 138/115; 138/128; 602/42; 277/946
(58) Field of Search .................. 602/42, 138, 264, 602/265, 523; 277/946, 935; 138/DIG. 3, 137, 129, 154, 156, 141, 114, 115, 128, 140

(56) References Cited

U.S. PATENT DOCUMENTS

| | | |
|---|---|---|
| 4,701,291 * 10/1987 | Wissman | 264/248 |
| 5,088,483 2/1992 | Heinecke . | |
| 5,194,335 * 3/1993 | Effenberger et al. | 428/421 |
| 5,197,976 3/1993 | Herweck et al. . | |
| 5,531,717 7/1996 | Roberto et al. . | |
| 5,560,986 10/1996 | Mortimer . | |
| 5,670,189 * 9/1997 | Dalton et al. | 425/371 |
| 5,676,688 10/1997 | Jaker et al. . | |
| 5,708,044 1/1998 | Branca | 521/145 |
| 5,972,441 * 10/1999 | Campbell et al. | 428/34.1 |
| 5,976,650 * 11/1999 | Campbell et al. | 428/35.7 |
| 6,007,488 12/1999 | Jaker et al. | 600/300 |
| 6,027,811 * 2/2000 | Campbell et al. | 428/411.1 |

OTHER PUBLICATIONS

Gabriele, M C; "Specialty Film Said to Yield High Dielectrical Properties," Modern Plastics International; (4) Apr. 26, 1996, p. 28/31.*

Jul. 2, 1996 New Release—Memcath™.

* cited by examiner

*Primary Examiner*—Dennis Ruhl
*Assistant Examiner*—Carie Mager
(74) *Attorney, Agent, or Firm*—Snell & Wilmer LLP

(57) ABSTRACT

A modified polytetrafluoroethylene resin membrane material is provided for a variety of medical or other applications. The material may be used as a bandage, tissue barrier, article covering or coating. Layers of the membrane may be combined to form tubes useful alone or tubes which can be combined with other tubes or manipulated.

6 Claims, 13 Drawing Sheets

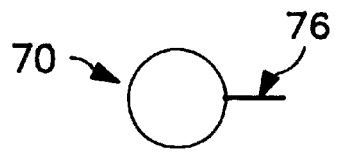
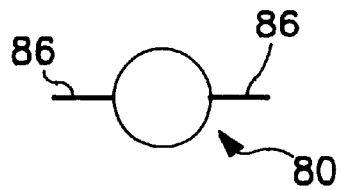
FIG. 5A    FIG. 6A
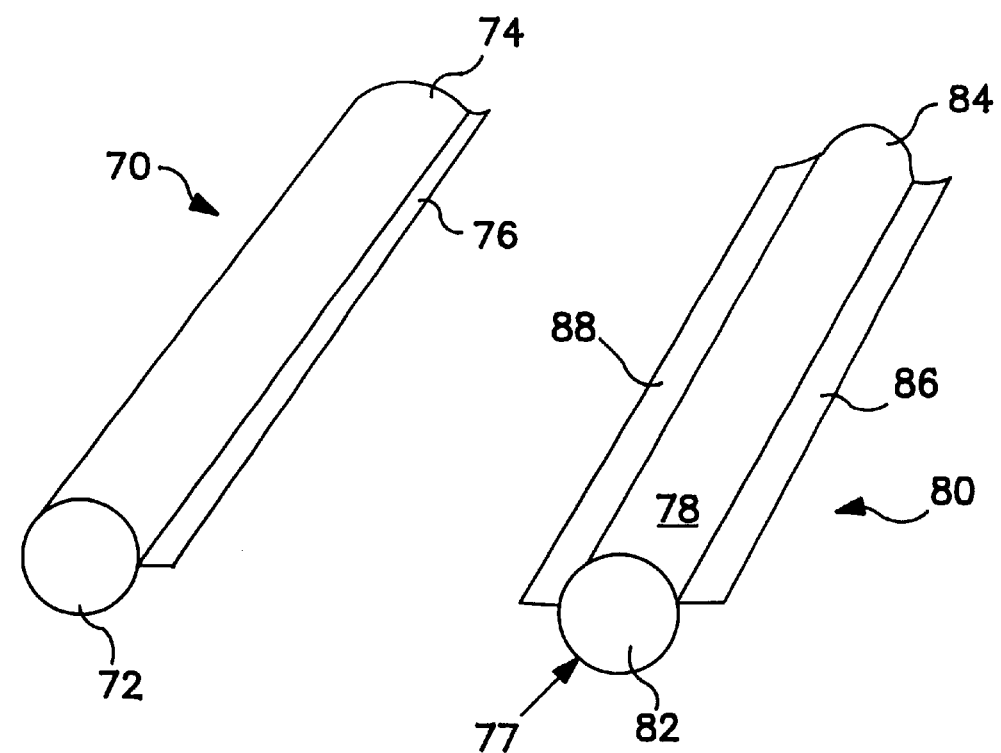
FIG. 5    FIG. 6

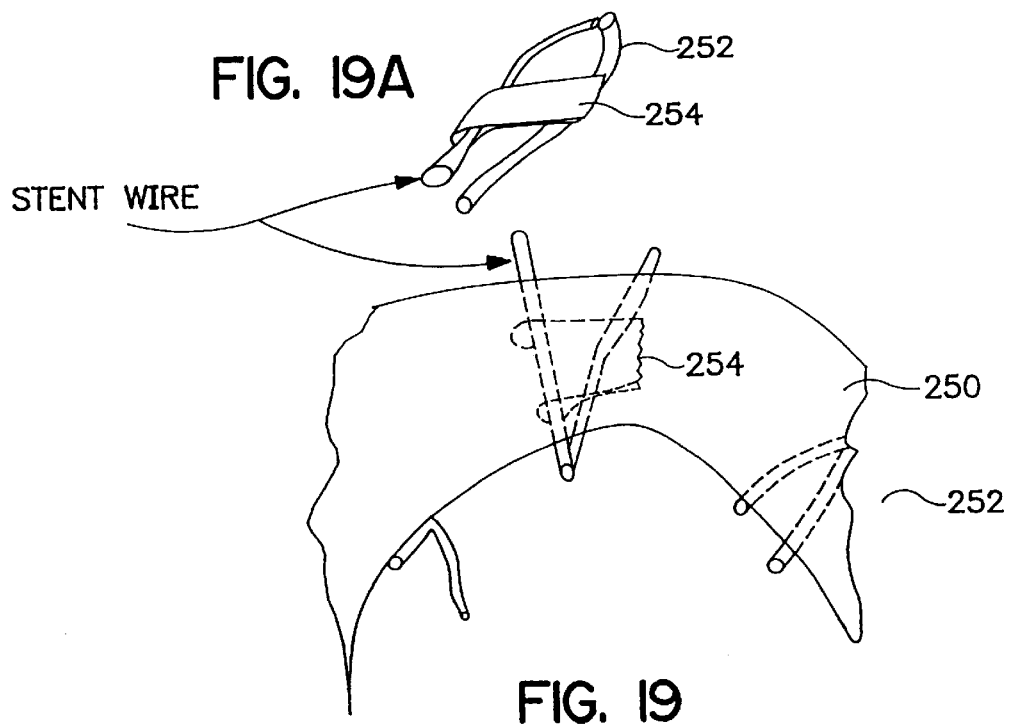
FIG. 19A
STENT WIRE
FIG. 19
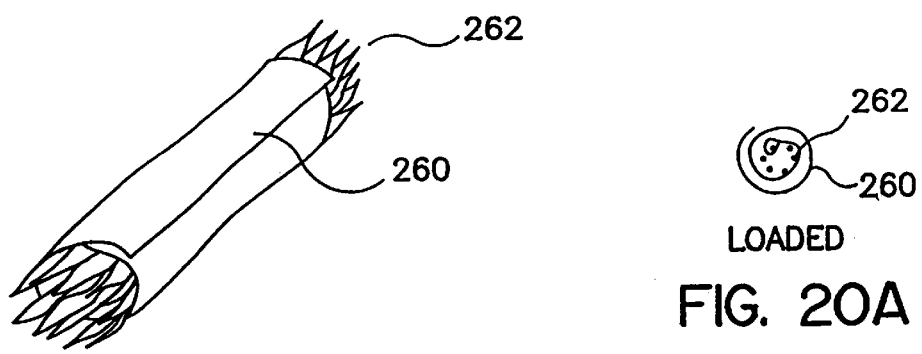
FIG. 20
LOADED
FIG. 20A
EXPANDING
FIG. 20B
FINAL
FIG. 20C

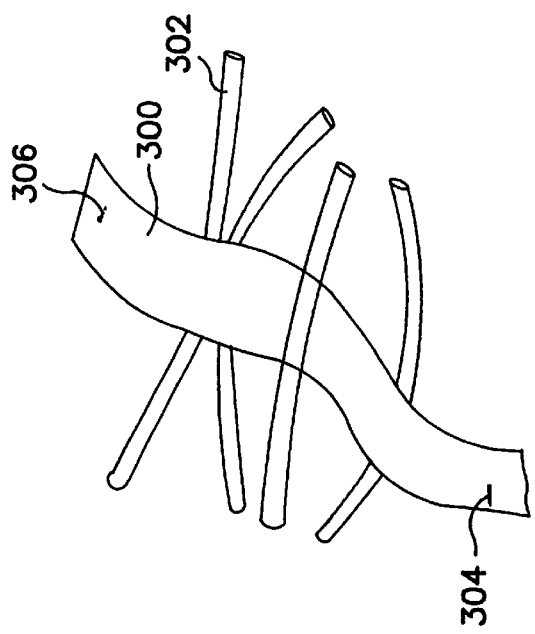
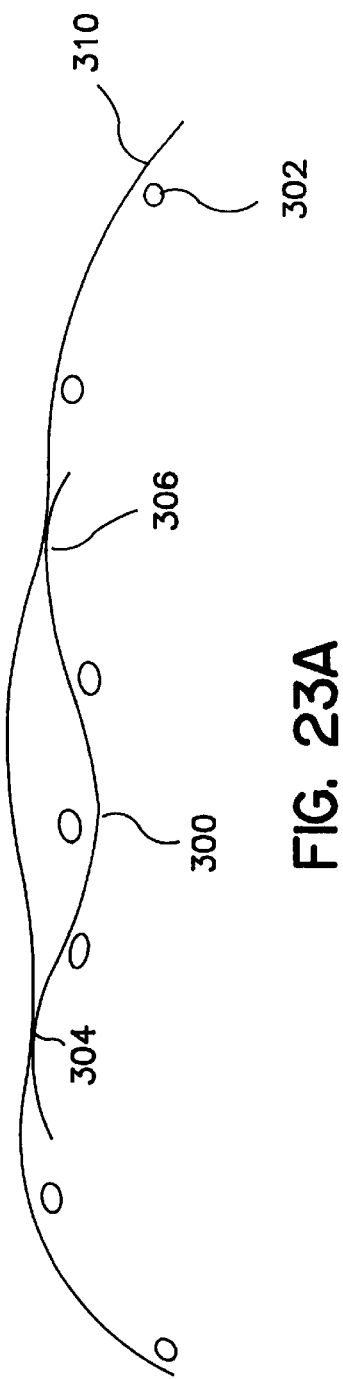
FIG. 23
FIG. 23A

MEMBRANES SUITABLE FOR MEDICAL USE

RELATED APPLICATIONS

The present application claims the benefit of a U.S. Provisional Application Ser. No. 60/023,405 filed on Aug. 14, 1996 and the U.S. Provisional Application Ser. No. 60/030,589 filed on Nov. 14, 1996, both of which are hereby incorporated herein by reference.

FIELD OF THE INVENTION

The present invention generally relates to a membrane material useful in connection with a variety of medical applications, and more particularly to materials useful in making medical articles, such as, bandages, membrane barriers, pouches, tubing and/or device coverings or coatings.

BACKGROUND OF THE INVENTION

There exists a long-felt need for an improved construction material useful in making and/or forming medical articles or covers for such articles. Specifically, presently known materials are generally not thin enough, strong enough, soft enough or pliable enough to be useful in connection with a wide variety of applications. For example, known tissue replacement devices including porous polytetrafluoroethylene (PTFE) or natural mammal (e.g. bovine) materials, while soft, often require significant volume, thus causing more pressure on the damaged tissue than is necessary. Moreover, currently available materials useful in constructing bandages, covers, tissue replacement devices, etc. suffer from a variety of other drawbacks.

In addition, many currently known medical articles could be improved with enhanced performance characteristics through coating of the devices and/or articles with a medically-acceptable membrane material. In accordance with the present invention, the term "coating" refers to materials which are applied to the article by application, dipping or other methodologies.

In addition, devices formed from materials which exhibit sufficient pliability, strength and minimal thickness and dimensions, such as, tubing for or medical or other use, would be desirable.

In general, there exists a long-felt and unresolved need for a thinner, softer, more slippery, non-porous material for medical and other applications.

SUMMARY OF THE INVENTION

While the present invention, in accordance with its various aspects, has a multitude of applications, in general, a specially formulated membrane material is provided which, utilized alone or with other devices, provides an enhanced product. In general, such enhanced products are suitable for medical uses, however, other industrial or commercial applications for such products as are now known or hereafter devised by those skilled in the art are contemplated by the disclosure and claims set forth herein.

One aspect of the present invention is a membrane constructed from a modified polytetrafluoroethylene ("PTFE") resin. The membrane is capable of being heat sealed to produce articles such as bags, sleeves, pouches, bandages and other articles having medical use.

In accordance with various other aspects of the present invention, the membrane may also be formed and shaped to suit a wide variety of medical applications. For example, the membrane can be heat sealed into structures such as pockets or sacks for cradling or isolating medical implant devices, organs or even other structures to contain bleeding. A variety of shapes and structures in various sizes can be fabricated from the membrane materials of the present invention.

In accordance with still other aspects of the invention, a preferred embodiment of the present membrane may function as a non-porous barrier between body fluids, tissues and/or organs. The non-porous property of the membrane may prevent bacteria from contacting and infecting tissue. Fluid and airborne bacterial contact may also be prevented by the membrane barrier.

Another beneficial property of a membrane in accordance with various aspects of the present invention is enhanced slip release. High slip release between the membrane and a contacting surface minimizes disturbance of healing tissues, thereby permitting faster recovery and reduced risk of infection. Stated another way, the membranes useful in the context of the present invention generally exhibit a non-stick property, such that they do not stick to weeping, healing wounds. Further, the membranes of the present invention may be used in sheet or fabricated form to cover and shield burns from ambient contaminants.

In accordance with various other aspects of the present invention, the membranes disclosed herein are suitably non-porous and non-occluding, thereby tending to inhibit thrombotic/clotting conditions in a patient. The non-occluding feature is further enhanced and distanced from currently available PTFE extrusion tubing through tensilization, which the aforementioned inventors have discovered greatly enhances slip performance.

In accordance with further aspects of the present invention, a membrane film constructed from a modified polytetrafluoroethylene resin has two ends, which are sealed producing a generally tubular body. The membrane is preferably formed from a sintered, tensilized, modified polytetrafluoroethylene resin. The resin may comprise a homopolymer which is modified with less than five percent of pertluoro propyl vinyl ether (PPVE).

Tensilizing stretches and densifies the polymer film such that the tensilized film has enhanced slip properties which reduces the friction co-efficient. Tensilizing also enhances the suppleness and softness properties of the film, while simultaneously increasing the linear strength.

In accordance with still further aspects of the invention, the membrane materials suitably formed into tubular bodies can include sections which are tensilized; for example, some sections may be less tensilized or non-tensilized. The present invention encompasses thin-walled, large and small diameter tubing which covers a broader range of diameters and thicknesses than current paste extruded PTFE, FEP PFA (fluorocarbon) tubing. Moreover, such tubes may be formed with single or double heat seals in a wide range of seal widths.

In accordance with yet further aspects of the present invention, such tubular bodies can be combined with other devices, such as one or more tubes (e.g., PVC tubes) to form other useful devices. In such cases, the present invention relates further to the method and apparatus for loading such devices into such tubes.

In accordance with various other aspects of the present invention, multiple membranes may be combined to form multi-layer and/or multi-lumen structures. Such structures may be useful alone or after further manipulation in accordance with the various methods set forth herein.

In accordance with yet other aspects of the present invention, membrane tubes formed in accordance with the present invention may be manipulated and/or combined with one another to form useful devices. Such manipulations may include further singular or multiple sealing operations and/or use with other devices.

In accordance with still further aspects of the present invention, the membrane materials useful in the context of the present invention can be used as coverings and/or coatings for other devices, such as stents, tubes, etc. As a stent covering, in accordance with various aspects of the present invention, the membrane materials disclosed herein may be used singularly or in conjunction with other membrane materials covering all or a portion of the stent or other devices.

Alternatively, and in accordance with yet further embodiments of the present invention, the stents or other devices useable in connection with the membrane materials disclosed herein, such as tubes or other devices, may be variously coated with the membrane materials to provide still further useful medical articles.

As will be described in detail in the following detailed description of preferred embodiments of the present invention, the methods, apparatus and devices of the present invention thus facilitate creation of useful articles suitable for a variety of medical applications. Such devices may be used in connection with surgical and/or non-surgical procedures, for insertion into body orifices, canals, wounds and/or other anatomical openings natural or man-made, Such devices as will be appreciated by the skilled artisan offer significant advantages over presently known devices made from presently known materials.

BRIEF DESCRIPTION OF THE DRAWING

Preferred exemplary embodiments of the present invention will hereinafter be described in conjunction with the appended drawing figures, wherein like numerals denote like elements and:

FIG. 5 shows a perspective view of a tube section formed of a membrane in accordance with the present invention having a single seal;

FIG. 5A shows a cross-sectional view of the tube section shown in FIG. 5;

FIG. 6 shows a perspective view of a tube section formed of a membrane in accordance with the present invention having a double seal;

FIG. 6A shows a cross-sectional view of the tube shown in FIG. 6;

FIG. 19 shows a further embodiment of a stent covering in accordance with the present invention wherein a portion of a stent is wrapped with a portion of a membrane sheet and other portions of the stent are suitably wrapped with other membrane sheets;

FIG. 19A shows an perspective view of the attachment mechanism of the stent covering shown in, for example, FIG. 19;

FIG. 20 shows a perspective view of still a further embodiment of a stent covering in accordance with the present invention wherein a membrane sheet is wrapped over the stent;

FIG. 20A shows a cross-sectional view of the stent covering of FIG. 20 in a "loaded" position;

FIG. 20B shows a cross-sectional view of the stent covering of FIG. 20 in an "expanding state";

FIG. 20C shows a cross-sectional view of the stent covering of FIG. 20 in a "fully expanded state";

FIG. 23 shows an exploded perspective view of an attachment mechanism useful in securing a stent covering of the type shown in FIG. 23A to a stent;

FIG. 23A shows a side view of yet a further embodiment of a stent covering in accordance with the present invention;

DETAILED DESCRIPTION OF THE PRESENT INVENTION

As previously noted, the form of the medical articles fabricated substantially from the membranes in accordance with the present invention alone, or in conjunction with other devices is varied. For example, the membrane materials disclosed herein may be used as artificial tissue devices, bandages, wound coverings, barriers, pouches, tubing materials, vascular grafts, coverings for other devices such as stents and the like or coatings for other devices such as tubes, pipes and the like to name just a few. Other applications for the materials and devices shown and described herein, which illustrations and descriptions are provided as exemplary embodiments of the present invention, are likely to be appreciated by the skilled artisan and are contemplated by the claims appended hereto.

Figure 1:
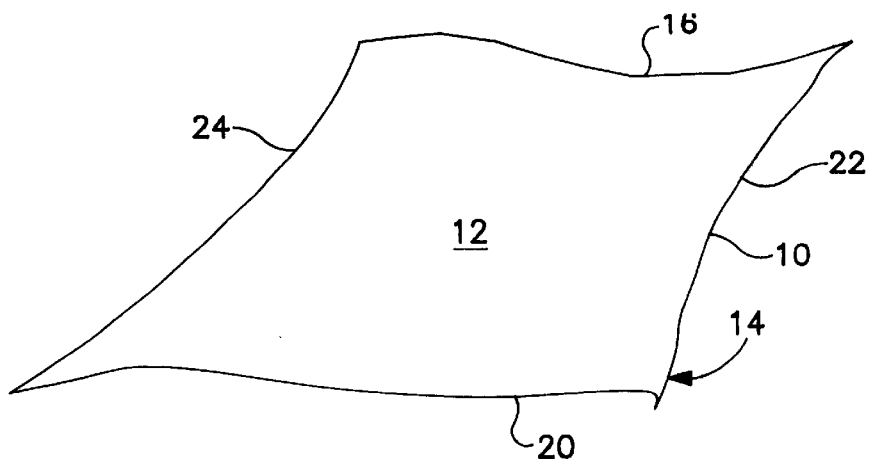
FIG. 1 shows a membrane sheet in accordance with the present invention.

Referring first to FIG. 1, a sheet 10 of a suitable membrane material can be described as having a first surface 12, a second surface 14, a first edge 16, a second edge 20, a third edge 22 and a fourth edge 24. Respective edges 16, 20, 22 and 24 can be suitably formed in any geometric configuration and can include additional edges. In their simplest form, such as is shown in FIG. 1, edges 16 and 20 are generally parallel and edges 22 and 24 are generally parallel, each of such edges exhibit a generally linear configuration. Membrane 10, as will be described more fully herein, may be used alone or in conjunction with other devices to provide a variety of useful articles.

The material useful in forming membrane 10 suitably comprises a polytetrafluoroethylene resin, a modified PTFE resin, and/or combinations thereof. In accordance with a particularly preferred aspect of the present invention, the membrane material is formed from a sintered PTFE film formed by skiving it off a billet. The PTFE billet preferably comprises a modified PTFE resin, such as, for example, Hoechst TFM 1700 or TFB 1702 available from DeWall Industries of Saunderstown, Rhode Island under the names DW/200 and DW/220 respectively. Such material comprises a modified PTFE polymer suitably modified by the addition of a small amount of perfluoro propyl vinyl ether (PPVE). In a preferred embodiment the addition of PPVE causes the PTFE to be more amorphous and/or more plasticized than pure crystalline PTFE. Such modification also permits the film to be heat sealed upon itself by, for example, interfacial fusion. Moreover, the modified material is substantially chemically inert.

It should be appreciated that other PTFE films may be suitably used in the context of the present invention as may be now known or hereafter devised by those skilled in the art. For example, PTFE homopolymers or co-polymers with co-monomers like PPVE, PFA and the like may be suitably used in accordance with various aspects of the present invention.

In accordance with a further preferred aspect of the present invention, the membrane material may also comprise a modified PTFE resin available from DuPont under the name Mitsui-DuPont TG 70-J which has been sintered into billets, annealed, and skived to a predetermined thickness.

The modified PTFE polymer resins useful in accordance with the present invention generally exhibit a low friction co-efficient in a "dry" state. In addition such resins are preferably capable of exhibiting heat sealing properties to the films and/or membranes formed thereof (i.e. interfacial fusion). The modified PTFE resins are also preferably non-porous, slippery and soft properties, as will be described herein, which are extremely beneficial in accordance with the various uses contemplated for the devices of present invention.

The membrane materials useful in accordance with the present invention also have use in connection with various catheter designs, such as those described in U.S. Pat. No. 5,531,717 issued Jul. 2, 1996 and the divisional application Ser. No. 08/629,109 filed Apr. 8, 1996, the descriptions contained in each of those references are hereby incorporated herein by reference.

Figure 4:
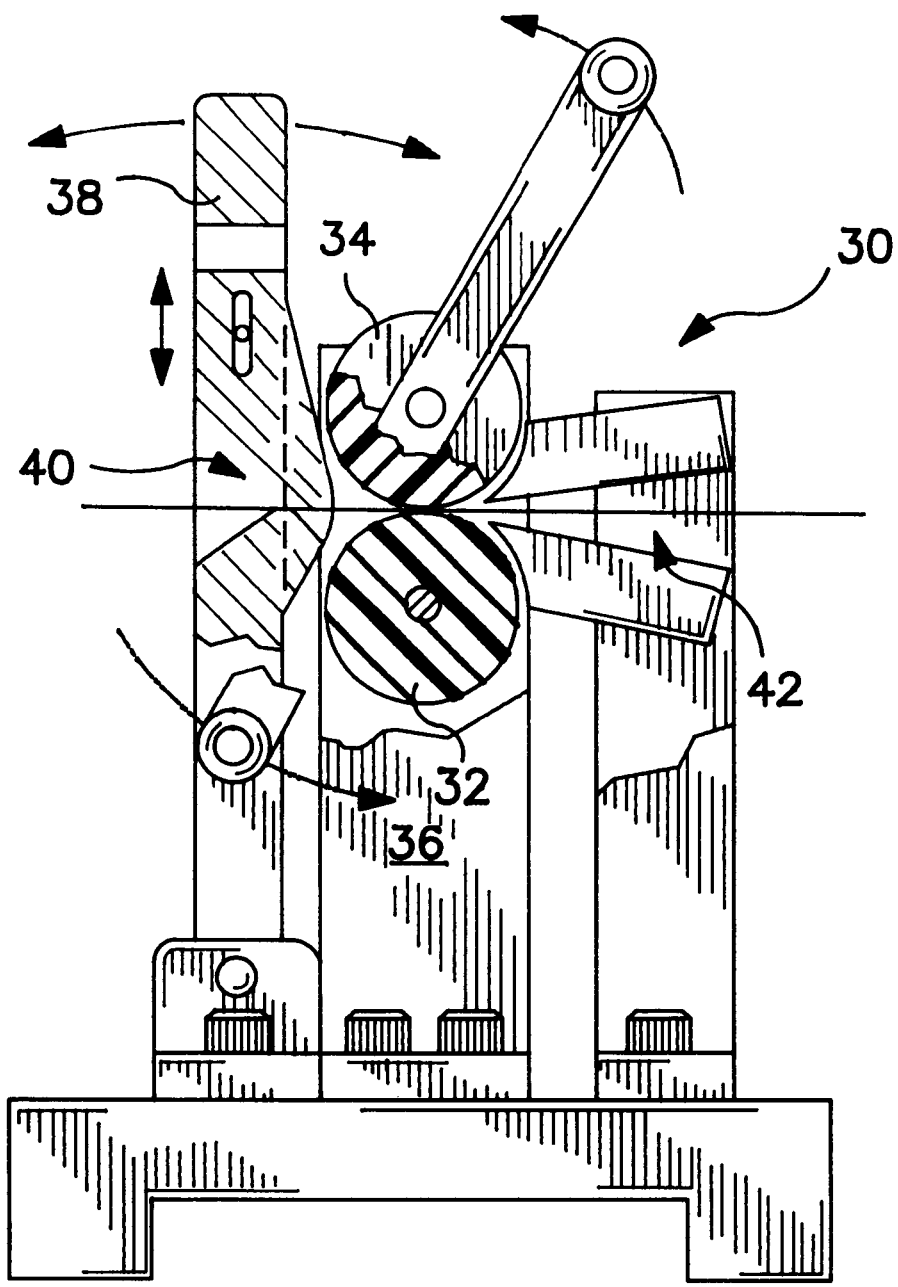
FIG. 4 shows a cut-away view of a tensilizing fixture useful for tensilizing the membrane materials or other articles formed thereof in accordance with the present invention.

The membranes useful in accordance with the present invention, such as membrane 10, can be modified to improve the strength and flexibility of the membrane. For example, as is described in the U.S. Pat. No. 5,531,717patent, membrane 10 may be suitably tensilized. Particularly, with momentary reference to FIG. 4, a suitable tensilizing fixture 30 may be utilized for such purpose. As shown in FIG. 4, fixture 30, preferably comprises two rollers 32, 34. A frame 36 secures rollers 32, 34. Each of the rollers 32, 34 are interference-fit under a load on the order of 50 pounds. Manual operation of a handle 38 engages and rotates the rollers 32, 34, thereby drawing and working membrane 10 through the juncture. As membrane 10 is drawn, a concurrent force is applied to a trailing edge elongating the membrane 10. That force may be applied manually or by using mechanical meterized assistance (not shown).

As shown in FIG. 4, an inlet 40 and an outlet 42 are defined by fixture 30. Preferably, membrane 10 advances while simultaneously being clamped and pulled backward at a force and rate so as to stretch and tensilize the film. As the film 10 advances between the rollers 32, 34 it extends through outlet 42. In the context of the present invention, tensilization of the membrane material (e.g. membrane 10) results in elongation from about 25 to about 300%, more preferably from about 50 to about 200% and optimally from about 125 to about 150% of the membrane material or article/device formed thereof.

Although a pin roller device, such as fixture 30 is preferred, the membrane materials useful in the context of the present invention can be tensilized using other known methods, such as by hand, manually or by automatic mechanisms. It should be appreciated that tensilization of the membrane materials useful in accordance with the present invention may be accomplished in any of a variety of ways, such as through the use of any conventional or hereafter devised method. It is believed that such tensilizing operations longitudinally strengthen the membrane film and lower the frictional coefficient by cold-flow molecular orientation of the membrane film. Annealing methods at 300–500° F. may also relieve some or most fabrication stresses.

The membrane materials in accordance with the present invention preferably exhibit a thickness (i.e. the thickness between surfaces 12 and 14) of less than about 0.010 inch, more preferably less than about 0.004 inch, still more preferably less than about 0.0025 inch, and even more preferably less than about 0.001 inch. For certain applications, a membrane in accordance with various aspects of the present invention may evidence a film thickness of about 0.001 to about 0.002 inches. At such dimensions the membrane is generally soft and supple. It should be appreciated, however, that depending upon the particular application for which membrane 10 is configured, as will be described in greater detail herein below, the particular dimensions of membrane 10, specifically the particular thickness of membrane 10 may be modified as desired.

Figure 2:
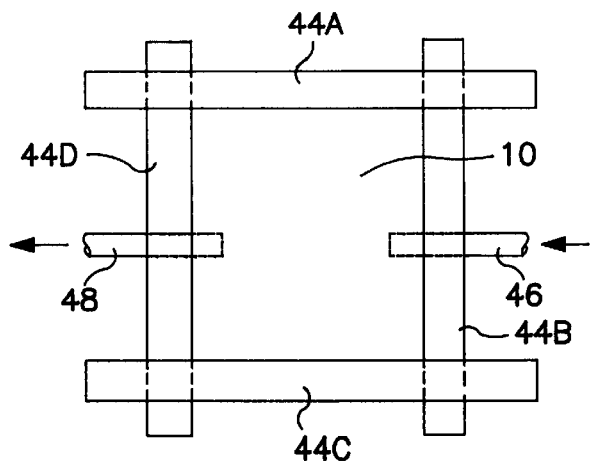
FIG. 2 shows a top view of a membrane sheet of the present invention taped over an area, for example in the region of a burn or wound, having an inlet vent and outlet vent.

In accordance with one embodiment of the present invention, membrane 10 may be applied to and/or on the epidermal skin layer of a patient. Referring now to FIG. 2, a membrane 10 may be suitably applied to and/or on the skin layer of a patient (not shown) and suitably secured to the skin layer through the use of respective strips of adhesive material 44A–D applied to respective edges 16, 20, 22 and 24. Other modes of adhering membrane 10 to and/or on the skin of a patient may also suitably be utilized. For example, in lieu of strips 44A-D, membrane 10 may be configured in the shape of a conventional bandage or wound dressing material with adhesive material applied over the top of and/or extending around the membrane in a manner suitable to adhere the membrane to the patient.

In the configuration shown in FIG. 2, membrane 10 suitably serves as a bandage or wound covering, and in such configuration may be suitably used in a vented or alternatively used in an unvented fashion. The membrane preferably is extremely lightweight and semi-transparent. Thus, damaged tissue is visible without the membrane being removed by health care personnel. Membrane 10 in such a configuration offers additional advantages over presently known materials in that the material exhibits high slip release, thereby minimizing disturbance of the healing tissues and/or wound, permitting enhanced recovery and reducing the risk of infection.

With continued reference to FIG. 2, tissue/membrane 10 interface may be vented. In accordance with this aspect of the present invention, once membrane 10 is suitably in place, the temperature and oxygen content of the tissue/membrane interface can be controlled by passing a purified filtered air oxygen mixture through a tubing inlet 46 located between membrane 10 and the patient's skin, or alternatively through an aperture formed in membrane 10. Preferably, the membrane/tissue interface is also vented through an opposing outlet tube 48. As a result, airborne bacteria is removed isolated from near the wound (e.g. damaged tissue) and the oxygen flow tends to accelerate healing thereby reducing infections. The oxygen feed may be combined with ultrasonic vaporizers and atomizers containing antibiotics and drugs that help penetrate the wound, thus also tending to increase the rate of healing.

Figure 2A:
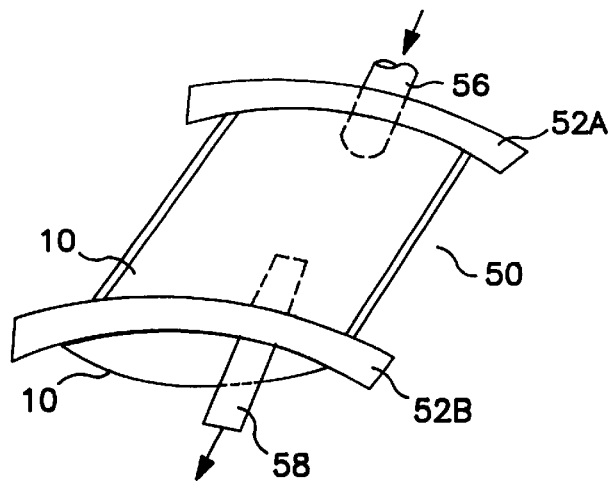
FIG. 2A shows a perspective view of a membrane sleeve of the present invention taped over an area, for example in the region of a burn or wound, having an inlet vent and outlet vent.

Referring now to FIG. 2A, in accordance with yet another embodiment of the present invention, multiple membranes 10 may be suitably joined to form a sleeve-like configuration, such as sleeve 50 shown. Sleeve 50 may be formed by suitably adhering respective edges, such as edges 22 and 24 of facing membrane materials 10 to each other by sealing (e.g. heat-sealing) and/or use of suitable adhesives. Use of multiple membranes 10 in this fashion enables the combined membranes to envelope a body extremity, such as a finger, arm, leg or other appendage. As with membrane 10 shown in FIG. 2, the edges of the sleeve 50 may be suitably adhered to the extremity such as through the use of adhesive strips 52A, 52B. In addition, the tissue region covered by sleeve 50 may be vented. In such case, preferably an inlet tube 56 and an outlet tube 58, configured similarly to inlet 46 and outlet 48 described in conjunction with FIG. 2, are suitably positioned to facilitate temperature and/or oxygen content at the affected and covered region. Sleeve 50 may also be used in an unvented fashion (not shown).

Although not shown in FIG. 2A, sleeve 50 may also be suitably inverted to reverse the heat-sealed seams prior to securing sleeve 50 about and/or onto an extremity of a patient. For certain applications, it may be desirable to seal a further edge of sleeve 50 such as to form a finger-cap and/or the like. With use of membrane 10 as shown in either FIG. 2 and/or FIG. 2A, suitable antibiotics or other dressing materials may be used in conjunction with the material.

In accordance with another embodiment of the present invention, the membrane material may be used within a patient's body. For example, a suitably configured membrane may be suitably implanted for the purpose of isolating body tissues, organs, or bone from the surrounding environment or for use as a tissue replacement article. Such isolation may be useful after a surgical procedure to promote healing and prevent fusing of natural tissue. Furthermore, the membrane may promote rebuilding and recovery due, in part, to its nonporous property.

Preferably, for such isolation uses, the membrane materials useful in the context of the present invention exhibit a porosity of less than 5/sq. in. at 0.001 inches or less. Porosity of course, may depend upon the thickness and level of tensilizing.

Figure 3:
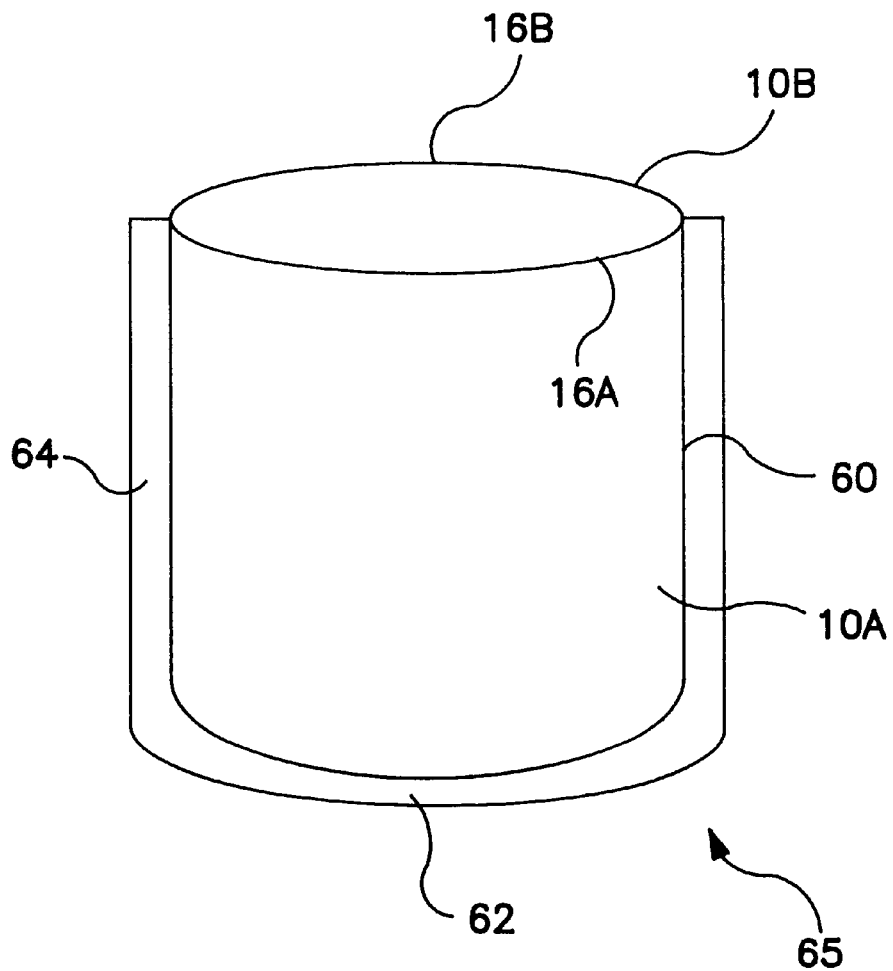
FIG. 3 shows a perspective view of a membrane pouch or bag in accordance with the present invention.

With reference now to FIG. 3, a pair of membrane sheets 10A and 10B are suitably joined together such that three of the respective four edges of each of the sheets are adhered or sealed together. In general, in accordance with this aspect of the present invention, a pouch (bag) may be formed. As shown in FIG. 3, a pouch 65 may be formed by joining together two membrane layers, one on top of the other, such that several edges are suitably sealed. Specifically, a membrane 10A is suitably arranged over a membrane 10B, such as shown in FIG. 3, and the respective edges 14, 20, 24 thereof (as shown in FIG. 1) of each layer are heat sealed together. As shown in FIG. 3, respective edges 16A (of membrane 10A) and 16B (of membrane 10B) are suitably not sealed to form an opening between membranes 10A and 10B. Similarly, and as is shown in FIG. 3, the edges which are sealed suitably form respective sealed edges 60, 62, and 64. Once sealed, any excess material is trimmed by conventional methods thus producing pouch 65. If desired, the pouch 65 can be inverted to put the sealed edges 60, 62 and 64 suitably inside of pouch 65 thereby formed.

In accordance with the various aspects of the present invention, the sealed edges, for example edges 60, 62 and 64 of pouch 65, can be formed in any conventional manner, for example through use of heat-sealing bars, sonic welding, use of a heat gun, a sintering oven, a thermal impulse, a hot iron, a hot bar or rollers, and or any other now known or hereafter devised combination of heat and pressure. In accordance with such embodiments, the respective edges of membranes 10A and 10B that are to be sealed are brought to a gel temperature of about 600–800° F. at a sufficient pressure for sufficient dwell time. The dwell time and pressure are dependent upon the film thickness as well as whether a tack weld or fusion weld is desired. The sealed edges or seals useful in the context of the present invention can vary, but typically are on the order of about 1/64 to about 1/2 of an inch for most applications.

Pouch 65 may be suitably used for surgical and/or laboratory isolation of tissues, body components or other articles. For example, pouch 65 may be suitably configured to cradle, wrap, cover or isolate a medical implant device, such as a stent, or in other applications to contain bleeding in traumatic surgery situations. Moreover, although not shown in FIG. 3, pouch 65 may be provided with one or more tabs for attaching the pouch to other structures and/or for closing the normally open end of pouch 65.

In accordance with yet another embodiment of the present invention, multiple membranes 10 may be suitably joined to form a tubular body. Such tubular bodies may have broad applications for medicine to industry. Moreover, such tubular bodies may be useful for a peristaltic pumps.

For example, with reference to FIGS. 5 and 5A, a tube 70 preferably comprises a generally cylindrical conduit having a first end 72, a second end 74 and a single sealed edge 76 extending along a longitudinal side thereof. For most applications, the walls of tube 70 preferably have a thickness less than about 0.010 in., and more preferably less than about 0.0025 in., and still more preferably less than about 0.001 inch. It has been found that one way of forming tube 70 is by folding a membrane layer (e.g. membrane 10) on top of itself to suitably form a tube. Preferably, in such case the edges are placed on top of each other, and the longitudinal edges thereof heat sealed to form edge 76.

With reference to FIGS. 6 and 6A, a tube 80 preferably comprises two membrane layers 77, 78 which are heat sealed along two of their respective edges, for example in a conventional manner, to form tube 80 having a first end 82, a second end 84 and respective sealed edges 86, 88. Once edges 86, 88 of tube 80 are suitably formed, excess material may be trimmed, and a tube cut to a desired length.

Tubes 70 and 80 may be suitably tensilized to improve the strength, slipperiness and flexibility thereof. As those skilled in the art will appreciate, tensilizing of polymeric films can be accomplished in a variety of ways. In accordance with the present invention, tensilizing can be accomplished before and/or after forming tubes 70 and 80 through any conventional or hereafter devised method. In some cases tensilizing after tube formation will be desired, and a tensilizing fixture, such as that shown in FIG. 4, may be employed. In accordance with a preferred aspect of the present invention, the tube so formed in accordance with the present invention is preferably elongated from about 25 to about 300%, more preferably from about 50 to about 200%, and optimally from about 125 to about 150%.

When tubes 70 and/or 80 are to be tensilized after formation of the tube from membrane material useful in accordance with the present invention, in certain applications it may be desirable to tensilize portions of the tube and leave other portions of the tube untensilized. For example, with reference now to FIG. 7, leading edge 82 of tube 80 is preferably not tensilized, whereas the remainder of tube 80, including trailing edge 84, is tensilized. By not tensilizing the portion surrounding the leading edge 82, leading edge 82 tends to exhibit a greater axial strength, and thus, can be more easily sized and ultimately attached to mating tubes, fittings and/or other devices. Preferably, in accordance with use of fixture 30 of FIG. 4, leading edge 82 is fed through rollers 32, 34 and no drag pressure is exerted on leading edge 82 so that it remains non-tensilized.

The tubular bodies formed in accordance with the present invention may also be further treated to obtain other beneficial properties. For example, the tubular bodies disclosed herein, such as tubes 70 and/or 80, may be suitably heat annealed to enhance axial burst pressure resistance. 30 In this regard, most axial burst pressure, for most tubes, is restored from the linear molecular orientation stresses by heat annealing the formed tubing at about 300° F. to about 500° F. for a period of time (ranging from a few seconds to a few minutes), while leaving in tact most of the reduced friction performance characteristics obtained through tensilization. In some cases, however, fracture and/or splitting of the two may be desirable (not shown), for example, as a desirable bio-engineering feature, as with some current cardio-vascular introducers. In such case, the tubes so formed can be provided with a small cut or other slit in the desired direction and location of the desired tear. In such case, when axial pressure is applied longitudinal tearing will initiate at such point and continue to a prescribed distance thereby allowing a tear or rip to be formed in the side of the tube.

Figure 7:
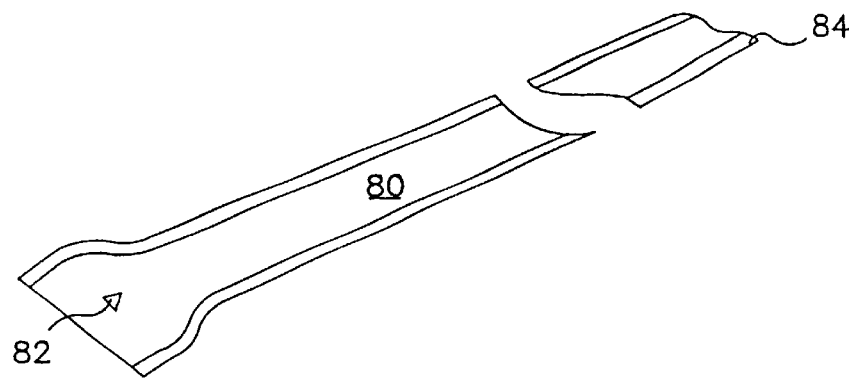
FIG. 7 shows a perspective view of a tube, of the type shown in FIG. 6, wherein a leading edge portion of the tube section is non-tensilized and wherein a trailing edge portion of the tube is tensilized in accordance with the present invention.
Figure 8:
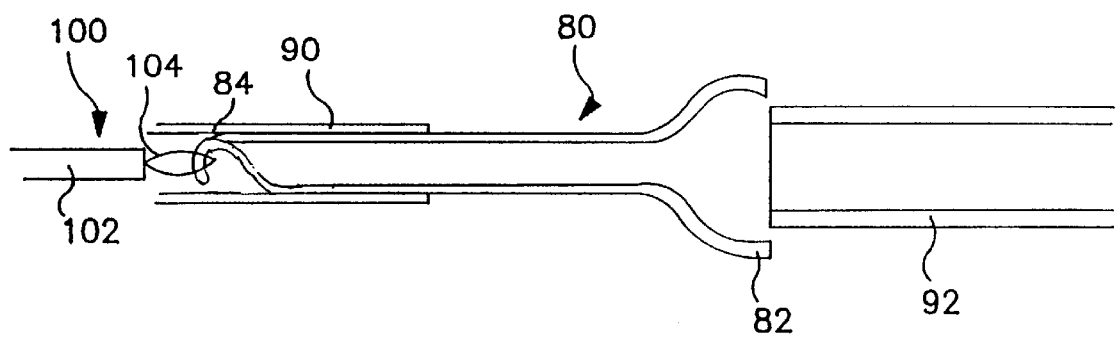
FIG. 8 shows a partial cross-sectional view of the tube of FIG. 7 with the tensilized trailing edge being inserted into a first tubing material and a second tubing material being inserted into the non-tensilized leading edge of the tube.
Figure 9:
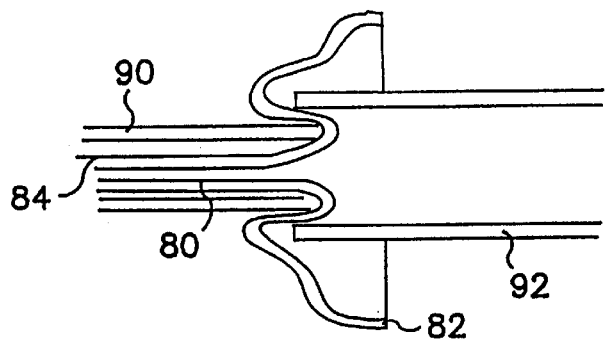
FIG. 9 is a partial section view showing the device of FIG. 8 wherein the respective tubing materials have been manipulated such that the first tubing material is positioned inside the second tubing material.

With reference now to FIGS. 8 and 9, a tube which is partially tensilized and partially not tensilized, such as shown in FIG. 7, may be used and connected to respective pieces of other tubing materials. For example, with reference to FIG. 8, a first tube 90 can be suitably configured to receive trailing edge 84. Tube 90 may be formed of any suitable material (e.g. polyvinyl chloride) and a second tube 92 exhibiting a larger internal diameter than tube 90 can be received in leading edge 82 of tube 80. As shown best in FIG. 9, tubes 90 and 92 can thereafter be manipulated such that tube 90 is worked interiorly of tube 92 so that a multi-layer multi-tube device is obtained. Such device may be used as a probe, introducer, catheter, balloon or other device. Such balloon device is described in more detail in U.S. patent application Ser. No. 08/676,581, the entire contents of which is hereby incorporated herein by reference.

As shown in both FIGS. 8 and 9, trailing edge 84 can suitably be threaded through the interior lumen of tube 90 by the use of a threading device 100. As shown, threading device 100 suitably comprises a rod 102 and a hook 104, hook 104 being suitably configured to receive an edge, for example trailing edge 84, of tube 80.

Figure 10:
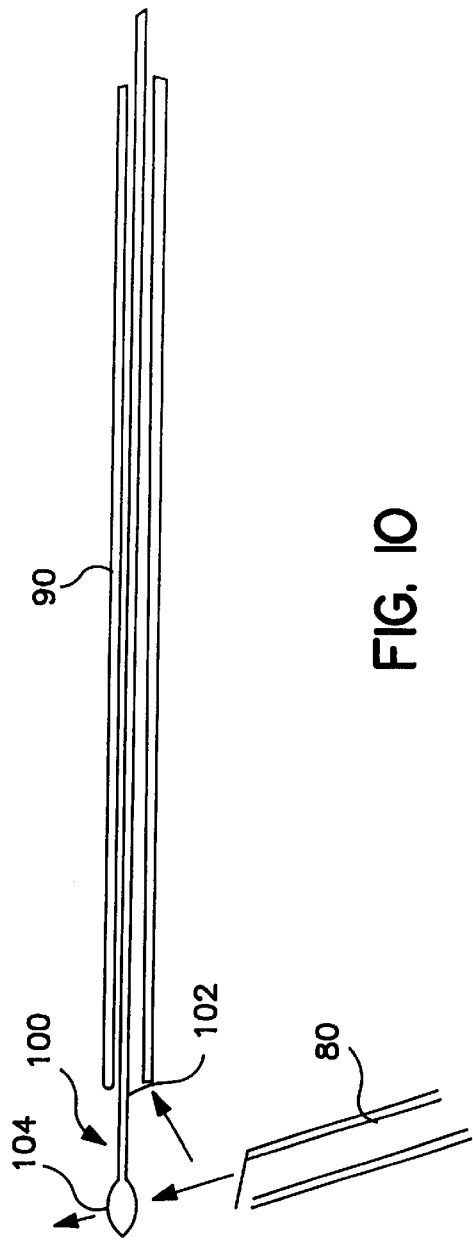
FIG. 10 shows a loading device for loading a formed membrane device, of the type, for example, as shown in either FIG. 5 and/or FIG. 6, being loaded into a tubing material by a membrane loader.
Figure 10A:
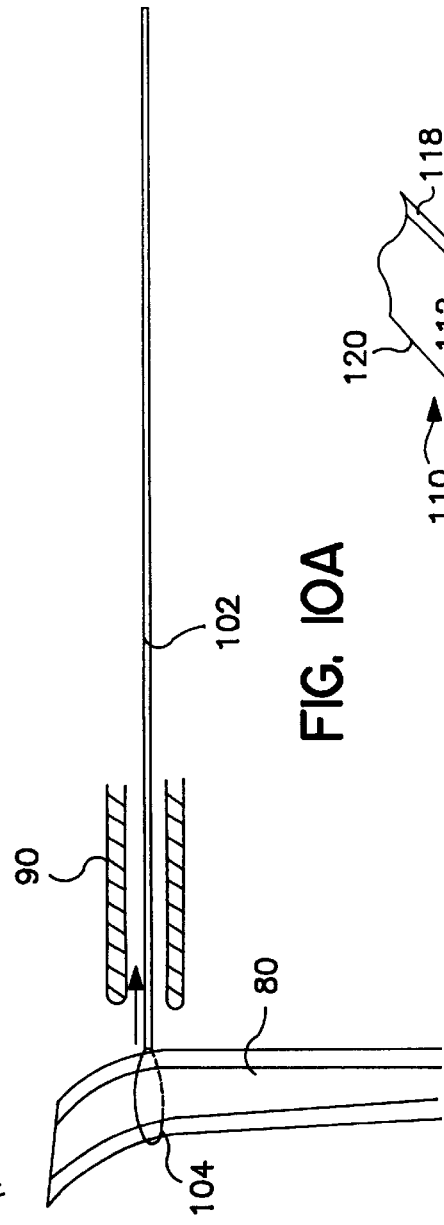
FIG. 10A shows a further view of the loading of such a formed membrane device into a tubing material in accordance with the present invention.

This threading process is shown in greater detail with reference to FIGS. 10 and 10A. Specifically, a tube, such as tube 70 and/or tube 80 may be suitably pulled through a wire loop pulling device 100 which is inserted through the interior lumen of an auxiliary tube, such as tube 90 and/or tube 92. Preferably, device 100 pulls tube 70 and/or tube 80 into the inner lumen of tube 90 and/or tube 92. If desired, device 100 can be used to suitably invert the membrane-formed tube within the lumen of the carrying tube.

Figure 11:
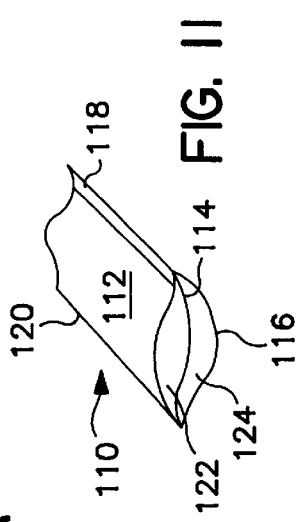
FIG. 11 shows a device formed of three membrane sheets in accordance with the present invention having a double outward seal.
Figure 12:
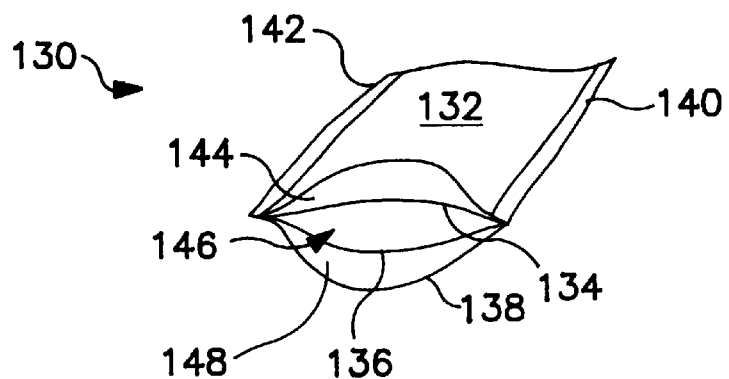
FIG. 12 shows a device formed of four membrane sheets in accordance with the present invention having a double outward seal.

Referring now to FIGS. 11 and 12, multi-layer and/or multi-lumen tubes may be formed in accordance with various aspects of the present invention. With specific reference to FIG. 11, in accordance with one embodiment of the present invention, three pieces of membrane material may be joined together to form a multi-lumen tube. Preferably, a first sheet of membrane material 112 is placed on top of a second piece of membrane material 114, which second piece 114 is in turn placed on top of a third piece of membrane material 1 16. The longitudinal edges of the composite structure, namely respective edges 118 and 120 are suitably heat-sealed, for example in a conventional fashion or in any other way as described above. As a result, a first lumen 122 is formed between juxtaposed layers 112, 114 and a second lumen 124 is formed between juxtaposed layers 114, 116. As with various of the previous constructs, multi-lumen tube 110 may be used in the form shown in FIG. 11, or alternatively, may be inverted, such as through use of pulling device 100 (see FIGS. 10 and 10A). In accordance with a particularly preferred aspect of this embodiment of the present invention, the various layers 112, 114 and 116 each are formed of tensilized membrane material having a thickness on the order of about 0.002 inch, and more preferably on the order of about 0.001 inch.

It should be understood that in accordance with various other aspects of the present invention, more than three layers of material may be used to form as many multi-lumen structures as may be desired for any particular application. For example, with reference now to FIG. 12, a tube 130 may be formed of four layers of membrane material, namely respective layers 132, 134, 136 and 138. Preferably, layers 132, 134, 136 and 138 are suitably sealed at, for example, respective edges 140 and 142 to form longitudinal seals about the length thereof. Such seals are suitably formed by, for example, heat-sealing as described hereinabove. As will be readily appreciated from FIG. 12, tube 130 provides a lumen between adjacent layers of material, namely a lumen 144 between juxtaposed layers 132 and 134, a lumen 146 between juxtaposed layers 134 and 136, and a lumen 148 between juxtaposed layers 136 and 138. In accordance with a particularly preferred aspect of this embodiment of the present invention, lumen 146 can suitably serve as a push rod sheath or introducer aperture.

Figure 12A:
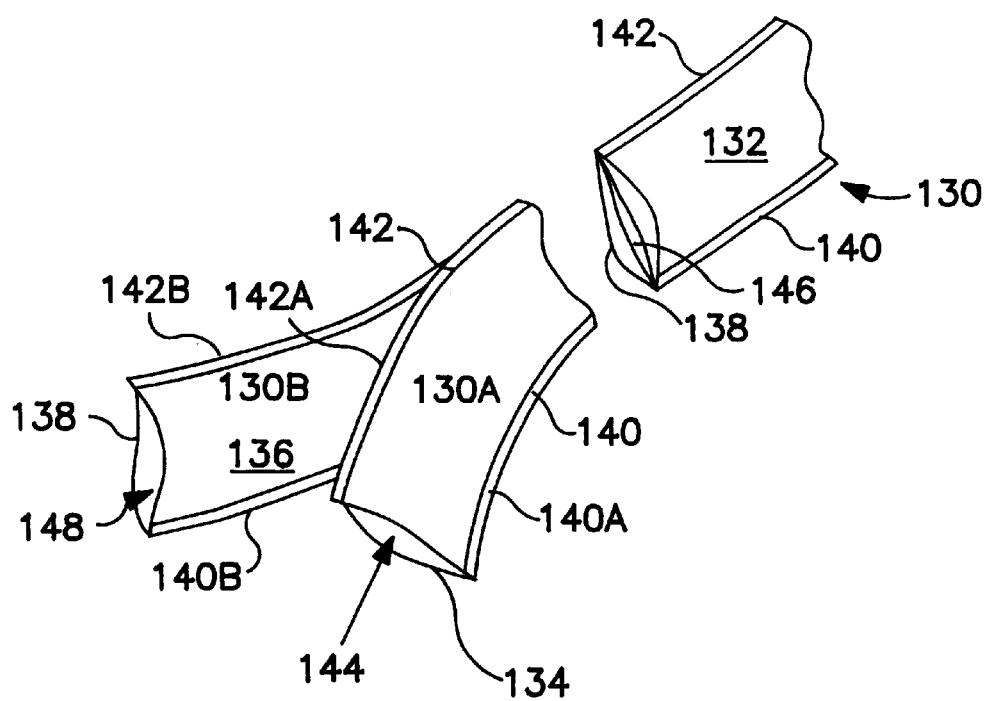
FIG. 12A shows a further embodiment of the device shown, for example, in FIG. 12, whereby two of the sealed membrane sheets are separated from the other two sealed membrane sheets at one end of the device.

Various modifications of tube 130 will be readily appreciated by those skilled in the art. For example, with reference now to FIG. 12A, tube 130 may be modified such that lumen 146 initiates at a portion spatially located away from the leading edge of the tube. Specifically, as shown in FIG. 12A, tube 130 can be suitably configured to have a leading edge comprising separate single lumen tubes, namely tubes 130A and 130B, which suitably communicate with tube 130, as shown. In such a configuration, lumen 144 initiates in tube 130A which is suitably comprised of the leading edges of layers 132 and 134. Similarly, lumen 148 is suitably formed by coupling of the leading edges of layers 136 and 138. As shown, layers 134 and 136 are not sealed together in proximity of the leading edge. In this fashion, tube 130A is provided with respective separately sealed edges 140A and 142A, and tube 130B is provided with respective separately sealed edges 140B and 142B. Respective edges 140A and 140B suitably communicate and terminate at edge 140, and respective edges 142A and 142B suitably communicate and terminate at edge 142. An instrument, such as a push rod and/or the like, may suitably be passed into lumen 146 between the juncture of tubes 130A and 130B.

Figure 13:
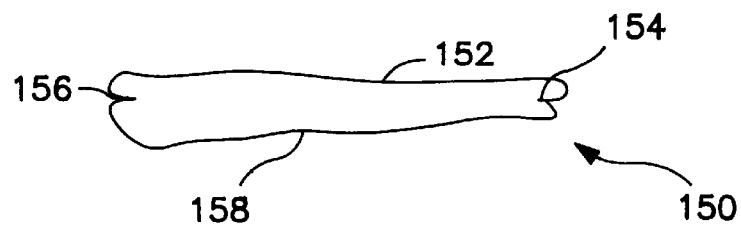
FIG. 13 shows a cross-sectional view of a tube of the type, for example, shown in FIG. 6 which has been inverted.

With reference now to FIG. 13, a tube, such as tube 80 as shown in FIG. 6, may be suitably inverted, that is, turned inside out, to form an inverted tube 150. As shown in FIG. 13, tube 150 suitably has a first layer 152 joined at its longitudinal edges 154 and 156 to layer 158. As previously briefly mentioned, inverted tube 150 may be separately used for various applications.

Figure 14:
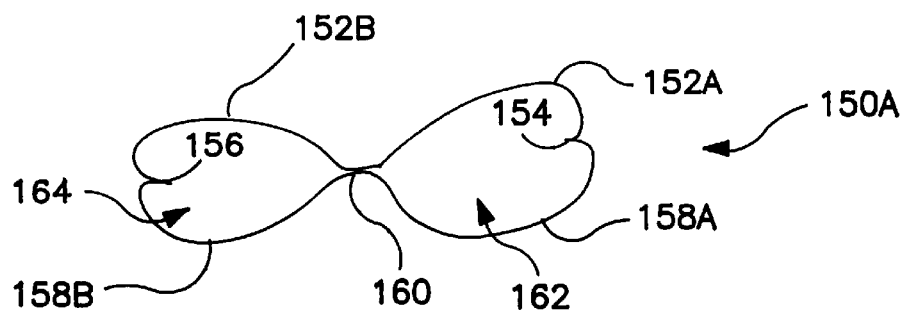
FIG. 14 shows a cross-sectional view of the tube shown in FIG. 13 wherein the central portion of the tube has been sealed upon itself.
Figure 15:
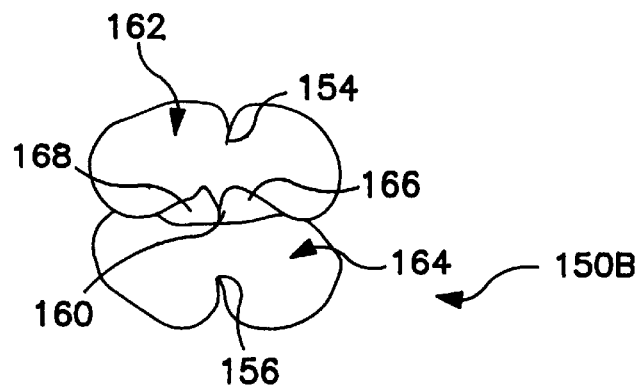
FIG. 15 shows a cross-sectional view of the device shown in FIG. 14 wherein the open ends of the device so formed are oriented one on top of the other.
Figure 16:
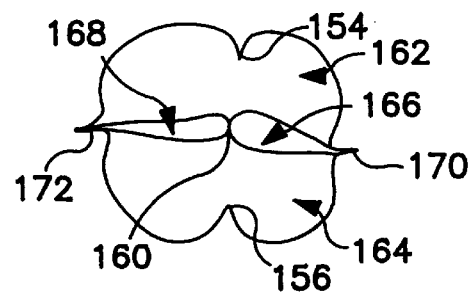
FIG. 16 shows a cross-sectional view of the device shown in FIG. 15 wherein the outer edges of such device have been sealed.

Alternatively, as shown in FIGS. 14–16, to which reference is now made, tube 150 may be manipulated to form a variety of different constructs. Specifically, with reference first to FIG. 14, a multi-lumen tube 150A may be formed simply by placing a seal 160 about the longitudinal axis of tube 150A. Seal 160 may be formed in any conventional manner, for example by heat sealing, and be variously configured to have any desired dimension. In such a configuration, respective apertures 162 and 164 are thereby formed in tube 150A. For certain applications, a multi-lumen tube of the type shown in FIG. 14, may be desirable over and/or used in place of the multi-lumen tube 110 shown in FIG. 11.

As shown in FIG. 14, aperture 162 is suitably formed by a portion 152A of layer 152 and a portion 158A of layer 158, with seals 160 and 154 forming the edges thereof. Similarly, aperture 164 is suitably formed by another portion 152B of layer 152 and another portion 158B of layer 158 with seals 160 and 156 forming the edges thereof. Although as shown in FIG. 14 apertures 162 and 164 preferably have similar dimensions, it should be appreciated that by locating seal 160 off of the longitudinal axis of tube 150, the dimensions of apertures 162 and 164 can be suitably altered. Stated another way, by moving seal 160 adjacent to edge 154, aperture 162 will decrease in size and aperture 164 will increase in size or vice versa.

With reference now to FIG. 15, manipulation of tube 150A can result in a further tube construct 150B. For example, as shown in FIG. 15, by orienting tube 150A such that edge 154 is located at the top and edge 156 is located at the bottom, apertures 162 and 164 can be suitably pressed together such that the outward edges and respective apertures 166 and 168 are thereby formed; preferably apertures 166, 168 are separated at the innermost portion by seal 160. If desired, in accordance with various aspects of this embodiment of the present invention, apertures 166 and 168 may be suitably maintained in that position by forming respective seals 170 and 172 (see FIG. 16) to enable formation of a further tube construct 150C. As shown in FIG. 16, tube construct 150C suitably comprises a quad-lumen tube formed of apertures 162, 164, 166 and 168.

Although the various manipulations shown in FIGS. 14–16 have been illustrated with reference to tube 150, similar to tube 80 shown in FIG. 6, it should be appreciated that various other constructs disclosed herein may also be similarly manipulated. or example, the multi-layer structures, namely tubes 110 and 130 shown in FIGS. 11 and 12, may be similarly manipulated. Further, it should be appreciated that multiple inverted tubes, such as tube 150, may be suitably combined to form various other multi-lumen constructs.

In accordance with various other embodiments of the present invention, the membrane materials disclosed herein may be suitably used as coverings and/or coatings for various other devices. For example, in the context of various surgical applications, stents are used to separate tissues, organs or other members for a variety of medical purposes. Such stents may be formed of plastic, metal or other materials and may exhibit a multitude of configurations. In accordance with various aspects of these embodiments of the present invention, the membrane materials disclosed herein are useful in covering such stents to render them more useful and offer significant advantages over currently available stents.

Figure 17:
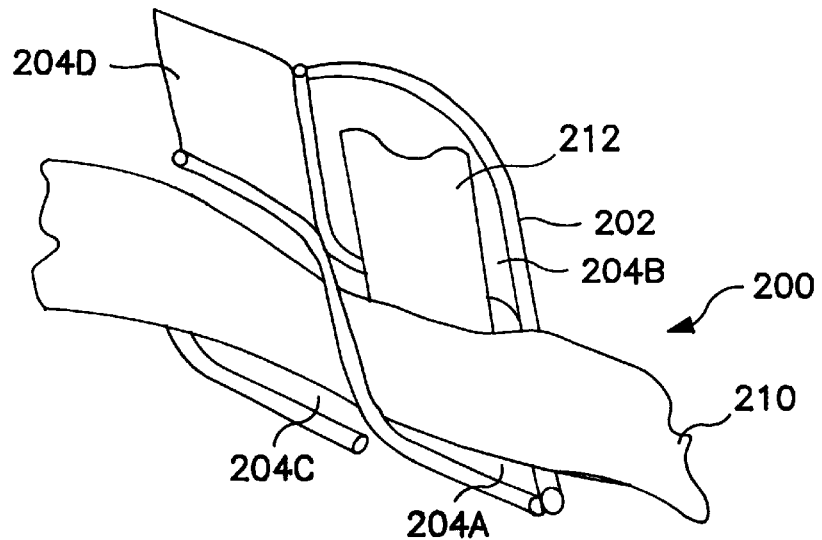
FIG. 17 shows a perspective view of a stent covering in accordance with one aspect of the present invention wherein multiple membrane sheets according to the present invention are weaved through apertures of a particular stent.

Referring now to FIG. 17, a stent structure 200, suitably comprising a frame member 202, typically formed of wire or other material, is configured to exhibit a number of openings. For example, with continued reference to FIG. 17, frame 202 shown therein is suitably configured to exhibit respective openings 204A, 204B, 204C and 204D. Preferably, to suitably cover portions of stent frame 202 various pieces of membrane material are simply weaved through the various apertures of frame 202. For example, with continued reference to FIG. 17, a first piece of membrane material 210 may be suitably weaved through apertures 204A and 204C. Similarly, a second piece of material 212 may be suitably weaved through apertures 204A and 204B. Of course, as will be appreciated, various other suitably sized and dimensioned pieces of membrane material may be weaved through the other apertures formed within stent frame 202 and various other weave paths or patterns can be used.

The various pieces of membrane material, namely pieces 210 and 212 may be suitably secured to the stent at the end thereof (not shown) by a spot weld or other adhesive. Preferably, an end of, for example, piece 210 may be wrapped around the end of the stent and heat-sealed upon itself to suitably secure that end of the membrane material to the end of the stent. Alternatively, a tab configuration (not shown) can be formed in the piece of material, the tab being suitably configured to enable attachment of the piece of material to stent frame 202. As will be appreciated by the disclosure just provided, various weaving patterns may be obtained through uses of various sized materials. For example, in certain applications, it may be desirable to weave more than one piece of material through particular apertures and/or particular series of apertures, as will be apparent to those skilled in the art from the disclosure just provided.

Figure 18:
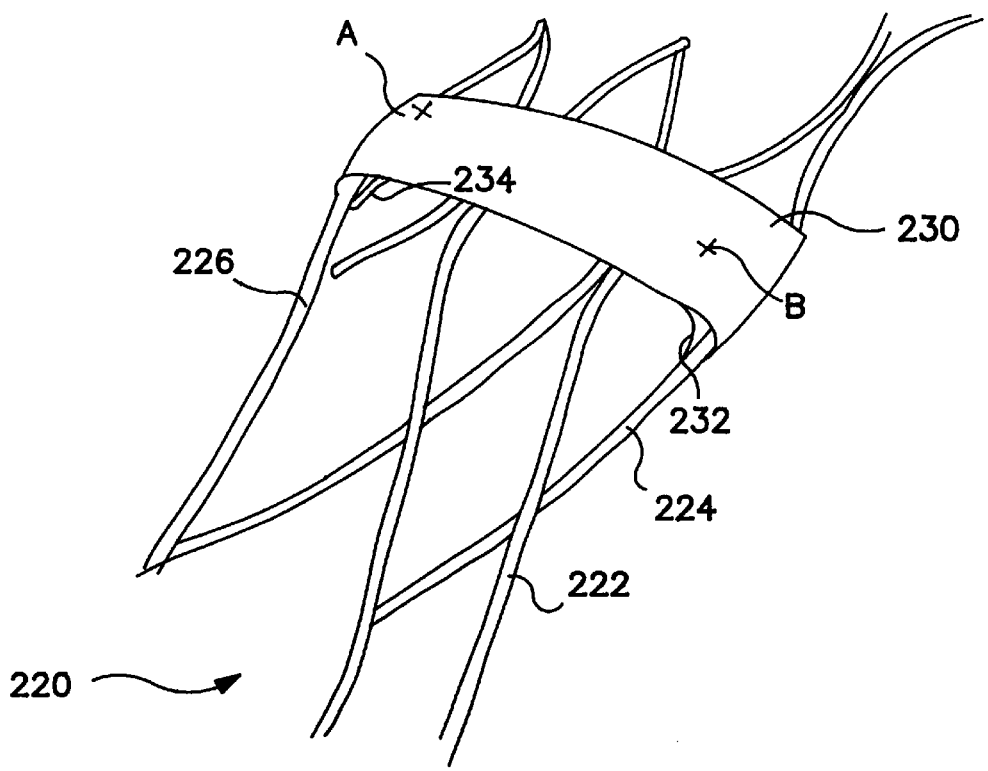
FIG. 18 shows a further embodiment of a stent covering in accordance with the present invention wherein a membrane sheet is wrapped over a portion of the stent so as to cover a portion of the stent, the ends of the membrane sheet being sealed upon itself surrounding still another portion of the stent.

Referring now to FIG. 18, a further embodiment of a stent covering in accordance with the present invention is shown. For example, a suitable stent structure 220 is formed by a frame 222 optimally configured to exhibit a plurality of openings. Frame 222, as shown, includes at least a first end frame member 224 and a second end frame member 226. In accordance with this aspect of this embodiment of the present invention, a suitably sized and dimensioned piece of membrane material 230 having a first end 232 and a second end 234 is suitably wrapped around stent frame 222. Preferably, and as shown in FIG. 18, first end 232 is suitably wrapped around member 224; similarly, second end 234 is suitably wrapped around member 226. Preferably, the respective ends of sheet 230 are suitably sealed to secure sheet 230 to stent frame 222. While various securement techniques may be used, spot welding techniques, such as through the application of heat at a particular spot along sheet 230 suitably are used. For example, as shown in FIG. 18, end 234 is tucked under frame member 226 and a suitable spot weld may be applied at point A. Similarly, end 232 is wrapped around member 224 and may be preferably folded back over itself and then spot-welded, for example, at location B to securely hold end 232 to stent frame 222.

Referring now to FIG. 19, a further embodiment of a stent covering in accordance with the present invention is shown. In accordance with this embodiment, a stent covering material 250 is suitably adhered to a stent frame 252 (shown only in part in FIG. 19), by a series of tabs 254 which are welded to portions of frame 252. With specific reference to FIG. 19A, a tab 254 is suitably welded to a portion of frame 252 so as to create a weld spot. Tab 254 suitably comprises a strip of a modified PTFE resin in accordance with the previously described materials. With continued reference to FIG. 19A, preferably, the strip is folded over a portion of stent 252 and then spot-welded to itself to form tab 254. Thereafter, and with reference again to FIG. 19, material 250 is suitably applied to stent frame 252. In a preferred embodiment, material 250 is adhered to frame 252 by spot-welding material 250 to the various tabs 254 contained on frame 252. Various advantages of this type of stent covering will be apparent to those skilled in the art. For example, covering stent frame 252 in this manner enables covering material 250 to be secured to and positioned with respect to frame 252, while at the same time allowing a certain degree of movement or float.

With reference now to FIG. 20, a further embodiment of a stent covering in accordance with various aspects of the present invention is disclosed. As shown best in FIG. 20, in accordance with this aspect of the present invention, a covering material 260 is suitably wrapped around a stent frame 262. In accordance with this aspect of the present invention, the covering material can be wound in any particular pattern, for example in a straight pattern, such as is shown in FIG. 20, or in a helical or any other pattern. As seen best in FIGS. 20A–C, in accordance with a preferred aspect of this embodiment of the present invention, covering material 260 is suitably wrapped about a portion of frame 262 to secure covering material 260 to frame 262. Any mode of attachment herein described or hereafter devised by those skilled in the art can be utilized. For example, tabs such as those shown in FIG. 19 may be utilized to secure covering material 260 to frame 262. By so wrapping frame 262 with material 260, a loaded position of stent frame 262, such as shown in FIG. 20A, can be obtained. Stated another way, covering material 260 can be suitably tensioned to draw frame 262 upon itself into a loaded position, thereafter, upon release of the tension, stent frame 262 can be caused to expand such as is shown in FIG. 20B, and ultimately to a final position such as is shown in FIG. 20C.

Figure 21:
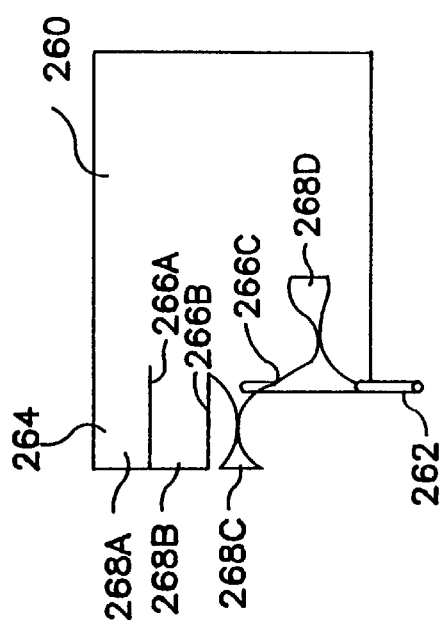
FIG. 21 shows yet a further embodiment of a stent covering in accordance with the present invention.

Alternatively, with reference to FIG. 21, preferably covering material 260 is suitably cut at one end thereof to form a plurality of tabs. In accordance with this alternative embodiment, a leading edge 264 of covering 260 is suitably provided with a plurality of slits 266A, 266B, 266C to form a plurality of tabs 268A, 268B, 268C and 268D in leading edge 264. Once the tabs are formed, the tabs may be twisted such as shown with respect to tab 268C to form a weld receiving position. With specific reference to tab 268D once the weld receiving position is formed, it may be suitably folded back onto the remaining portion of covering 260 over a portion of frame 262 and then spot welded to secure tab 268D securely to material 260, thereby securing material 260 to frame 262.

As will be appreciated by those skilled in the art, other stent covering forms will be apparent in view of the foregoing description. For example, although in accordance with particularly preferred aspects of the present invention the stent covering materials comprise the modified polytetrafluoroethylene resins described herein, it should be appreciated that in certain applications other materials may be suitably used. For example, in certain applications, thicker materials such as PTFE, urethane, foils (metal and otherwise) and multi-layer structures may suitably be employed as covering materials.

Figure 22:
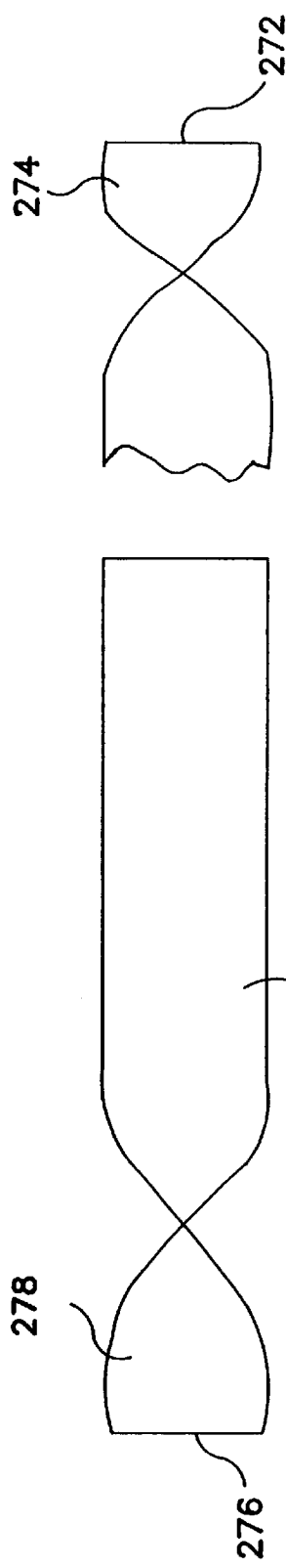
FIG. 22 shows yet a further embodiment of a stent covering in accordance with the present invention.

For example, an alternative embodiment of the stent covering shown in FIG. 20 in accordance with the present invention can be obtained by use of multiple coverings using a variation of the attachment mechanism shown in FIG. 21. For example, with reference to FIG. 22, one or more membrane materials 270 may be suitably formed such that at a leading edge 272 a tab 274 is formed. Preferably, tab 274 is formed by twisting leading edge 272 over an angle of 180° or more. Similarly, at a trailing edge 276, a tab 278 can be suitably formed in a like fashion. Material 270 can then be applied to a stent frame (not shown but similar to stent 262 shown in FIG. 20) such as by helically winding membrane 270 around the outer surface of the coiled frame. Material 270 may be secured to the frame by securing tab 274 at one end of frame and securing tab 276 at another end of the frame. In accordance with particularly preferred aspects of this embodiment of the invention, a further piece of material 270A may be suitably helically wrapped in a direction opposite the wrapping of material 270 and suitably secured to frame by attachment of tabs 274A and 276A to frame 280.

In the context of this embodiment of the present invention, it should be appreciated that tabs 274 and 278 may be suitably formed in other ways. For example, in lieu of twisting material 270 to form such tabs, material 270 could be cut (die-cut or otherwise) or suitably formed to exhibit such tabbed configurations.

With reference now to FIG. 23, another securement mechanism in accordance with various aspects of the present invention is illustrated. As shown in FIG. 23, in lieu of tabs 254 such as are illustrated best in FIGS. 19 and/or 19A, in accordance with this embodiment of the present invention a single piece of membrane material 300 is suitably weaved through a portion of a stent frame 302 to form respective weld locations 304 and 306. Such weld locations can be used, as shown best in FIG. 23A, to attach a covering material 310 to frame 302 by spot welding material 310 to weld locations 304 and 306 of material 300.

In accordance with a still further embodiment of the present invention, the resin material useful in accordance with the present invention in forming the various membranes and other constructs described herein may also be bonded to other surfaces. For example, the present inventors have found that the various resins described herein can be bonded not only to themselves, such as to form the various seals disclosed herein, but also to other suitable surfaces formed from metals, plastics, thermoplastics, rubbers, etc. For example, iron or copper pipe/tubing may be suitably enhanced for medical or industrial uses through use of an internal and/or external coating/covering of the membrane materials useful in the context of the present invention. In such cases, the membrane materials can be bonded to coated or uncoated surfaces of the pipe/tubing. Preferably, for certain applications, the pipe/tubing surfaces are coated with the same or similar resin material or other resin materials such as PFA, FEP, etc. Other devices/articles such as cylindrical polypropylene webs, woven polyester sleeves or porous PTFE grafts also can be coated with the resin materials disclosed herein.

In accordance with various aspects of this embodiment of the present invention, such bonding can be accomplished through the application of heat, which may be generated in any conventional manner, and/or sintering the film directly onto the pipe/tubing substrate. Some examples of heat generating sources include a sintering oven, a heat gun, radiant KL-rods, heat bars, rollers, RF seals sonic welding devices and/or various lasers, for example, $CO_2$ or Yag and/or the like.

Figure 24:
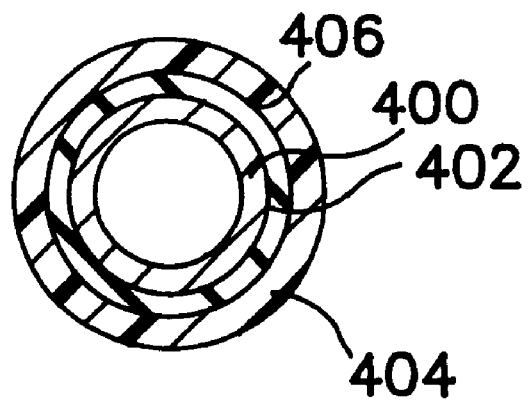
FIG. 24 shows a cross-sectional view of a tube coated with a material coating in accordance with the present invention.

A preferred embodiment of a coated structure in accordance with this aspect of the present invention is illustrated with reference to FIG. 24, wherein a metallic (e.g. copper, iron, etc.) rod 400 is suitably provided with a polymeric coating 402, and applied to coating 402 is a layer of membrane material 404. The juncture between layers 404 and 402 may be suitably joined by tack welds 406 or be continuously sealed about the entire length thereof. For example, a plurality of tack welds may be suitably formed through use of laser or sonic welding thereby, partially securing layer 404 to layer 402.

Figure 25:
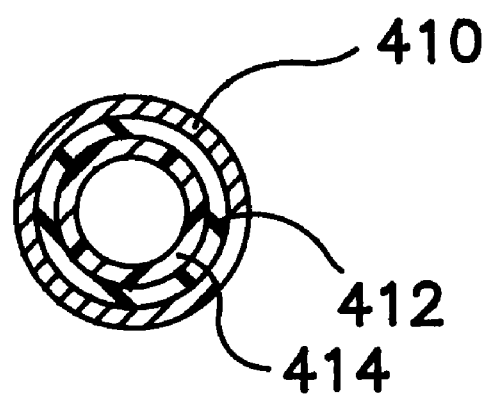
FIG. 25 shows a cross-sectional view of tube, the interior portions of which have been coated with a material coating in accordance with the present invention.

An alternative embodiment in accordance with this aspect of the present invention is shown in FIG. 25, wherein a layer of material in accordance with the present invention is preferably applied to the interior portion of a metal pipe 410. In accordance with a preferred aspect of this embodiment of the present invention, pipe 410 is first provided with a PFA, FEP, and/or the like emulsion coating, such as may be obtained by dipping pipe 410 into a desired FEP or PFA emulsion. As will be appreciated by those skilled in the art, pipe 410 can be suitably provided with such FEP coating 412 through any conventional dipping process. The present inventors have found that adhesion of the modified PTFE resin useful in the context of the present invention is enhanced through use of such a coating, however, it should be appreciated that a lining of the PTFE resin material may be provided to pipe 410 without use of the same. Nevertheless, as shown in FIG. 25, preferably a membrane material layer 414 is suitably secured about its entire length to layer 412. While the examples shown in FIG. 24 and 25 utilize a covering material applied to a metallic base material, it should be appreciated that various other devices or materials may be similarly coated with the materials described herein.

It will be understood that the above description is of preferred exemplary embodiments of the present invention, and that the invention is not limited to the specific forms shown and described herein. For example, some or all of the components may be modified and alternate configurations which are apparent to those skilled in the art can be made. In sum, various modifications may be made in the design and arrangement of the elements within the scope of the invention, as expressed in the appended claims.

We claim:

1. A multi-lumen tube comprising
   a first layer of a material formed of a modified polytetrafluoroethylene resin including less than 5% of perfluoro propyl vinyl ether,
   a second layer of a material formed of a modified polytetrafluoroethylene resin including less than 5% of perfluoro propyl vinyl ether, and
   a third layer of a material formed of a modified polytetrafluoroethylene resin including less than 5% of perfluoro propyl vinyl ether;
   wherein each of said layer includes first and second longitudinal edges, each of said first and said second longitudinal edges of each of said layers being heat-sealed about a portion of the length of said longitudinal edges.

2. The tube of claim 1, wherein said longitudinal edges are sealed about substantially the entire length thereof.

3. The tube of claim 1 further comprising a fourth layer of a modified polytetrafluoroethylene resin including less than 5% of perfluoro vinyl ether, said fourth layer including first and second longitudinal edges which are heat-sealed to said first and second longitudinal edges of at least said third layer.

4. The tube of claim 1, wherein a thickness of each of said layer is less than about 0.004 inches.

5. The tube of claim 1, wherein a thickness of each of said layer is about 0.0001 to about 0.002 inches.

6. The tube of claim 1, wherein said material is tensilized.

* * * * *